US011172815B2

(12) United States Patent
Magno et al.

(10) Patent No.: US 11,172,815 B2
(45) Date of Patent: Nov. 16, 2021

(54) UTERINE CAVITY BIOCOMPATIBLE SEAL (71) Applicant: Gyrus ACMI, Inc., Southborough, MA (US)

(72) Inventors: Joey Magno, Cordova, TN (US); Rachel M. McGuire, Cordova, TN (US); Eric A. Gilbert, Cordova, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 494 days.

(21) Appl. No.: 15/849,926

(22) Filed: Dec. 21, 2017

(65) Prior Publication Data

US 2019/0191985 A1  Jun. 27, 2019

(51) Int. Cl.
| *A61B 1/00* | (2006.01) |
| *A61B 1/32* | (2006.01) |
| *A61B 1/015* | (2006.01) |
| *A61B 1/303* | (2006.01) |
| *A61B 17/42* | (2006.01) |
| *A61B 17/12* | (2006.01) |
| *A61M 25/10* | (2013.01) |
| *A61B 17/32* | (2006.01) |
| *A61B 17/00* | (2006.01) |

(52) U.S. Cl.
CPC ............ *A61B 1/32* (2013.01); *A61B 1/00082* (2013.01); *A61B 1/00154* (2013.01); *A61B 1/015* (2013.01); *A61B 1/303* (2013.01); *A61B 17/1204* (2013.01); *A61B 17/32* (2013.01); *A61B 17/42* (2013.01); *A61B 17/4241* (2013.01); *A61M 25/10* (2013.01); *A61B 17/12136* (2013.01); *A61B 2017/00004* (2013.01); *A61B 2017/00557* (2013.01); *A61B 2017/00858* (2013.01); *A61B 2017/00902* (2013.01); *A61B 2017/4216* (2013.01); *A61B 2217/005* (2013.01)

(58) Field of Classification Search
CPC . A61B 1/303; A61B 2017/4216; A61B 17/42; A61B 1/00082; A61B 2018/00559; A61M 2210/1433; A61M 25/1002
USPC .................................................. 600/115–116
See application file for complete search history.

(56) References Cited

U.S. PATENT DOCUMENTS

| 8,409,109 B2 * | 4/2013 | Tiesma ..................... A61B 5/01 600/549 |
| 9,392,935 B2 | 1/2016 | Adams et al. |
| 2005/0234437 A1 * | 10/2005 | Baxter ............... A61B 18/1492 606/15 |
| 2005/0288551 A1 * | 12/2005 | Callister ............ A61B 1/00082 600/115 |

(Continued)

FOREIGN PATENT DOCUMENTS

| WO | 90/02525 | 3/1990 |
| WO | 2010/036721 | 4/2010 |

*Primary Examiner* — Alexandra Newton Surgan
(74) *Attorney, Agent, or Firm* — Schwegman Lundberg & Woessner, P.A.

(57) ABSTRACT

A method includes: delivering a biodegradable expandable member into a body cavity of a patient; insufflating the biodegradable expandable member in the body cavity to expand the body cavity; sealing the biodegradable expandable member against an inner wall of the body cavity to seal the body cavity internally; and delivering an endoscope into the body cavity.

11 Claims, 8 Drawing Sheets

(56) References Cited

U.S. PATENT DOCUMENTS

| | | | |
|---|---|---|---|
| 2006/0089658 A1* | 4/2006 | Harrington | A61B 17/12031 606/119 |
| 2009/0054868 A1* | 2/2009 | Sharkey | A61B 18/04 604/515 |
| 2012/0157981 A1* | 6/2012 | Evans | A61B 17/16 606/15 |
| 2016/0106466 A1 | 4/2016 | Gruber et al. | |

* cited by examiner

UTERINE CAVITY BIOCOMPATIBLE SEAL

BACKGROUND

Field of the Invention

The exemplary and non-limiting embodiments described herein relate generally to devices and methods that relate to hysteroscopic procedures for the removal of uterine fibroids and other abnormal gynecological tissues. The exemplary and non-limiting embodiments described herein relate more particularly to surgical procedures pertaining to hysteroscopic tissue removal systems having fluid management and/or monitoring capabilities.

BRIEF DESCRIPTION OF PRIOR DEVELOPMENTS

It is believed that uterine fibroids occur in a substantial percentage of the female population, perhaps in at least 20 to 40 percent of all women. Uterine fibroids are well-defined, non-cancerous tumors that are commonly found in the smooth muscle layer of the uterus. In many instances, uterine fibroids can grow to be several centimeters in diameter and may cause symptoms like menorrhagia (prolonged or heavy menstrual bleeding), pelvic pressure or pain, and reproductive dysfunction. Hysteroscopy may be performed in either a physician's office with or without local anesthesia or in the operating room under monitored anesthesia care (MAC) or regional or general anesthesia. Hysteroscopy has been shown to be a safe and effective method for the treatment of, for example, uterine adhesions, intrauterine septa, and abnormal uterine bleeding.

SUMMARY

In accordance with one aspect of the invention, a device comprises: an access sheath comprising a tubular member; an inflatable member coupled to the access sheath; and, an endoscope having a working channel, the endoscope being configured to be positioned through the access sheath. The inflatable member is configured to be received into a uterine cavity by insertion of the access sheath into the uterine cavity, and the inflatable member is configured to expand to cover a contour of the uterine cavity upon inflation and to internally seal the uterine cavity.

In accordance with another aspect of the invention, a method comprises: delivering a biodegradable expandable member into a uterine cavity of a patient; insufflating the biodegradable expandable member in the uterine cavity to expand the uterine cavity; sealing the biodegradable expandable member against an inner wall of the uterine cavity to seal the uterine cavity internally; and delivering an endoscope into the uterine cavity.

In accordance with another aspect of the invention, a method of treating a uterine abnormality of a patient comprises: inserting an access sheath having an inflatable member into a uterine cavity; providing an endoscope through the access sheath and into the uterine cavity, the endoscope having a working channel; inflating the inflatable member to expand the inflatable member and to cover a contour of the uterine cavity; and operating a medical device through the working channel of the endoscope to treat the uterine abnormality of the patient.

BRIEF DESCRIPTION OF THE DRAWINGS

The foregoing aspects and other features of the invention are explained in the following description, taken in connection with the accompanying drawings, wherein.

DETAILED DESCRIPTION

Hysteroscopy may be invaluable for diagnosing and treating the intrauterine cavity. Hysteroscopic procedures may be performed using an endoscope, with or without an attached integrated video imaging system, with the use of media suitable for distending the uterus. Examples of fluid media used to distend the uterus include, but are not limited to, liquids such as water or certain aqueous solutions (for example, a saline solution or Ringer's lactate solution) and gases. One exemplary method of distending the uterus using an appropriate gaseous medium involves insufflation with carbon dioxide ($CO_2$). Upon the distension of the uterus, the surgical procedure carried out may relate to hysteroscopic tissue removal such as the removal of uterine fibroids or other abnormal gynecological tissues.

Figure 1:
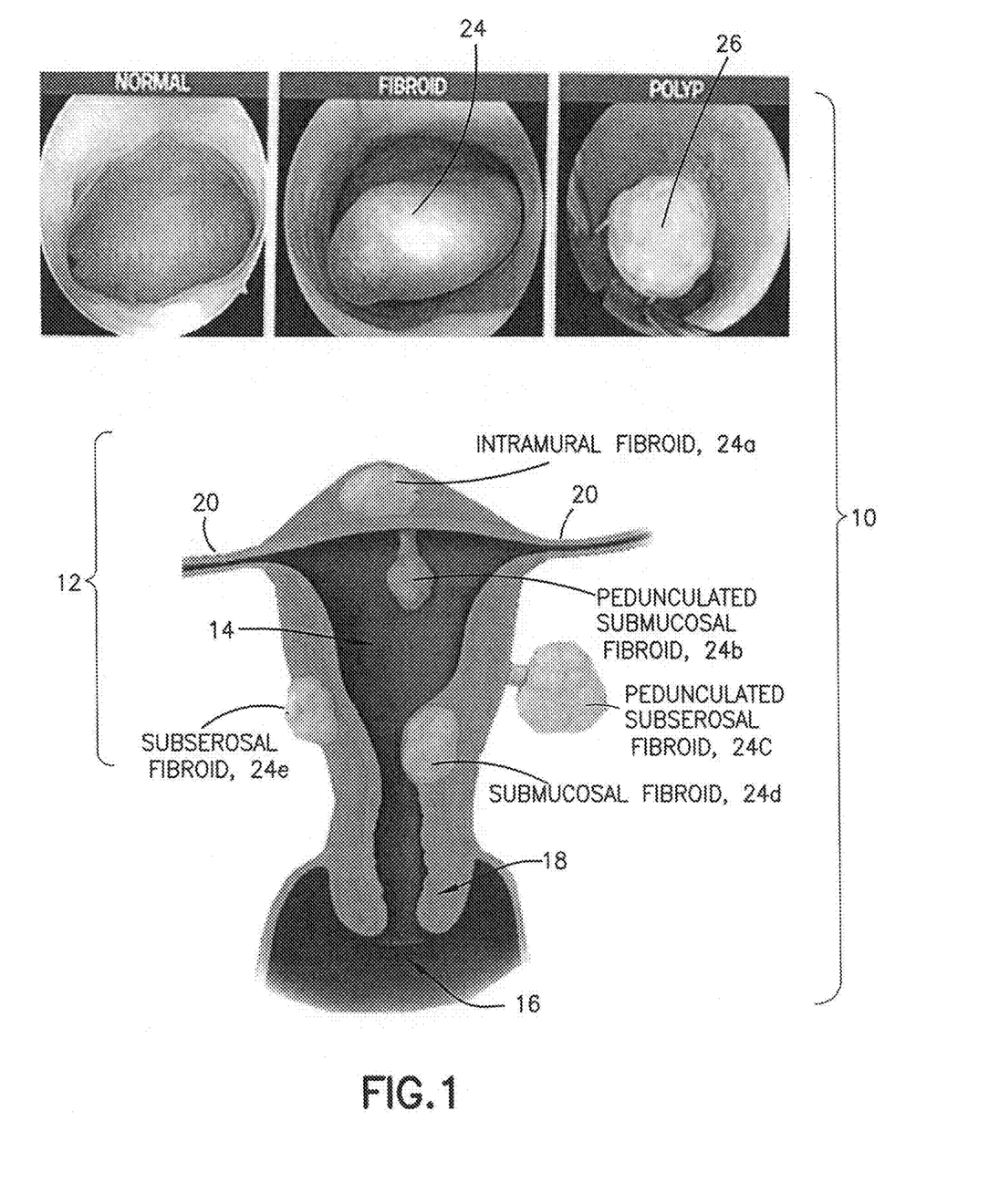
FIG. 1 is a schematic representation of a gynecological cavity having various tissue abnormalities.

Referring to FIG. 1, a gynecological cavity is shown and designated generally by the reference number 10. The gynecological cavity 10 includes the uterus 12 defining the uterine cavity 14, access to which is generally through the vaginal canal 16 and the cervix 18. The fallopian tubes 20 extend from an upper portion of the uterus 12 and terminate in fimbriated and funnel-shaped openings that wrap partway around the ovaries 22 (shown in FIG. 2).

It may be desirable in various situations for medical personnel to perform diagnostic and/or therapeutic procedures within the gynecological cavity 10. For example, as shown in FIG. 1, a surgeon may wish to detect, visualize, and/or treat conditions including, but not limited to, various tissue abnormalities such as fibroids 24, polyps 26, tumors, adhesions, or other tissue abnormalities within the uterus 12. Types of fibroids 24 include, but are not limited to, intramural fibroids 24a, pedunculated submucosal fibroids 24b, pedunculated subserosal fibroids 24c, submucosal fibroids 24d, subserosal fibroids 24e, and the like. The surgeon may also wish to treat endometriosis or other abnormal bleeding or fertility issues. To facilitate the visualization, detection, and/or treatment of the above and like conditions, ample space may be needed within the gynecological cavity 10 for the procedure to be performed. Unfortunately, however, in those instances in which the gynecological cavity 10 is the uterine cavity 14, adequate space does not typically exist naturally. This is because the uterus 12 is a flaccid organ. As such, the walls of the uterus 12 are typically in contact with one another when in a relaxed state (similar to the walls of a deflated balloon). Consequently, active steps are generally taken to create a working space within the uterine cavity 14. One technique for creating such a working space is to administer a fluid medium to the uterine cavity 14, transcervically, under sufficient pressure to cause the uterus 12 to become distended.

Fluid media administered to the uterus 12 can be of low or high viscosity and of low or high molecular weight. The fluid media can also be either electrically conductive or nonconductive based upon the presence or absence of electrolytes in the fluid media. In terms of gaseous fluid media, it is generally accepted that $CO_2$ can be used as a distending medium for diagnostic hysteroscopy only as it may not be suitable for operative hysteroscopy or diagnostic procedures due to possible bleeding and the collection of blood and tissue debris, which may obscure the optical field of a viewing apparatus.

Figure 2:
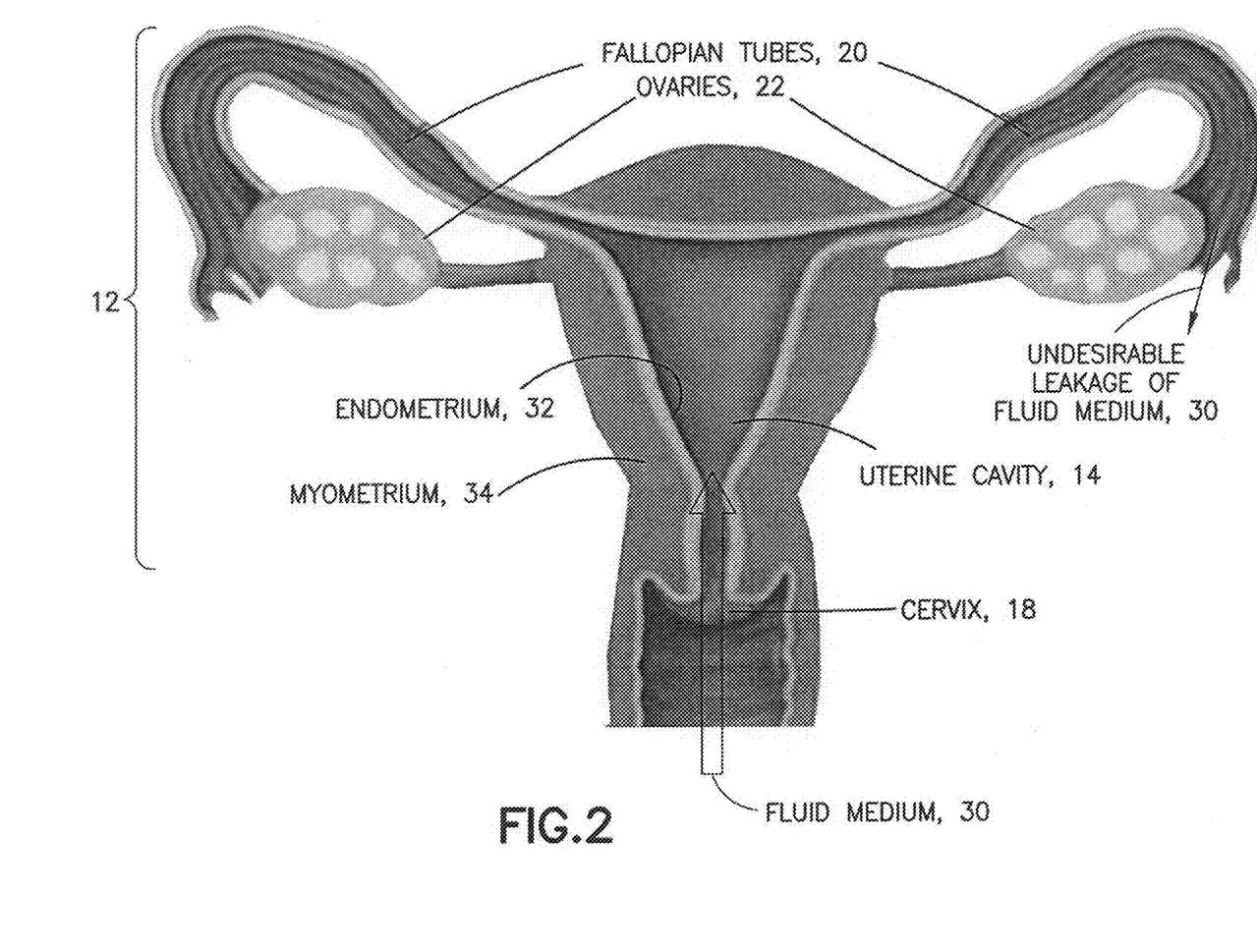
FIG. 2 is a schematic representation of uterus having a fluid medium introduced thereto.

Referring now to FIG. 2, the fluid medium, shown generally at 30, may be introduced into the uterus 12 to cause the distension. While useful for the performance of hysteroscopy and hysteroscopically directed procedures, the distending fluid medium 30, if absorbed systemically in sufficient amounts, may have adverse effects on a patient. Consequently, understanding the physical properties and the potential risks associated with the use of the various fluid media used for distending the uterus 12 is beneficial for the safe performance of hysteroscopic procedures. For example, because the fluid medium 30 is administered under pressure (which pressure may be as great as 80-100 millimeters (mm) Hg or greater), there may be a risk of intravasation. Intravasation during hysteroscopy procedures is the absorption of the uterine distension media through the uterine vasculature, thus resulting in such fluids leaking through open uterine channels such as the ostium of the uterine tube or the fallopian tubes 20 where the fluid is then spilled to the peritoneal or abdominal cavity. The methods as described herein allow for the minimization of fluid spillage and absorption in the patient's body. Factors influencing the amount of intravasation can include, but are not limited to, intrauterine pressure; number and size of the vascular openings in the uterus; duration of the procedure; and the condition of the patient. In other cases, the principal mechanism of systemic absorption of the distending fluid medium 30 may be directly related to surgical disruption of the integrity of the venous sinuses in the deep endometrium 32 and the myometrium 34. Whether due to intravasation or surgical disruption, when these vessels or sinuses are transected, the fluid medium 30 is provided an opportunity to access the systemic circulation if the uterine pressure is greater than the patient's mean arterial pressure (MAP). Fluid overload in the patient can cause pulmonary edema or other undesirable effects. In terms of large amounts of $CO_2$ absorption, $CO_2$ is highly soluble in blood and if sufficiently high amounts reach the systemic circulation of the heart, $CO_2$ embolism may present, which may result in cardiorespiratory collapse.

To minimize the opportunities for the fluid medium to access the systemic circulation, intrauterine pressure should be controlled (for example, by close monitoring of the fluids administered) to maintain a balance between too much pressure, which increases the opportunity for intravasation, and too little pressure, which decreases the visibility of the uterine cavity. The intrauterine pressure should remain below the patient's MAP. The MAP is the average pressure within an artery over a complete cycle of one heartbeat. Monitoring equipment in a hospital setting usually provides an automatic calculation of the MAP for the anesthesia personnel who can then report the reading to the operative team. In a physician's office, it may be necessary for medical personnel to manually calculate the patient's MAP using data from an automatic blood pressure monitor.

The AAGL (American Association of Gynecologic Laparoscopists) Practice Report Practice Guidelines for Management of Hysteroscopic Distending Media states:

"a. For healthy patients, the maximum fluid deficit of 1000 mL is suggested when using hypotonic solutions. This is based on a decrease in serum sodium of 10 mmol, with absorbed volume of around 1000 mL. The maximum limit for isotonic solution is unclear, but 2500 mL has been advocated in the previous AAGL Guidelines. Individualization and an opinion from an anesthesiologist should be obtained.

b. When high-viscosity distending media are used, the maximum infused volume should not exceed 500 mL, and in the elderly and those with cardiopulmonary compromise should not exceed 300 mL."

There are cases where hysteroscopic procedures are aborted due to a large fibroid 24 that needs to be removed but the fluid deficit was reached. The fluid deficit is characterized by the difference between the volume of distension fluid instilled into the uterine cavity 14 and the volume of, fluid removed through the out-flow channel of a hysteroscope, plus fluid collected from the drapes or inadvertently lost in drapes and surrounding area of the operative table. The deficit closely represents the amount of fluid that may have been absorbed into the patient's vasculature.

Figure 3:
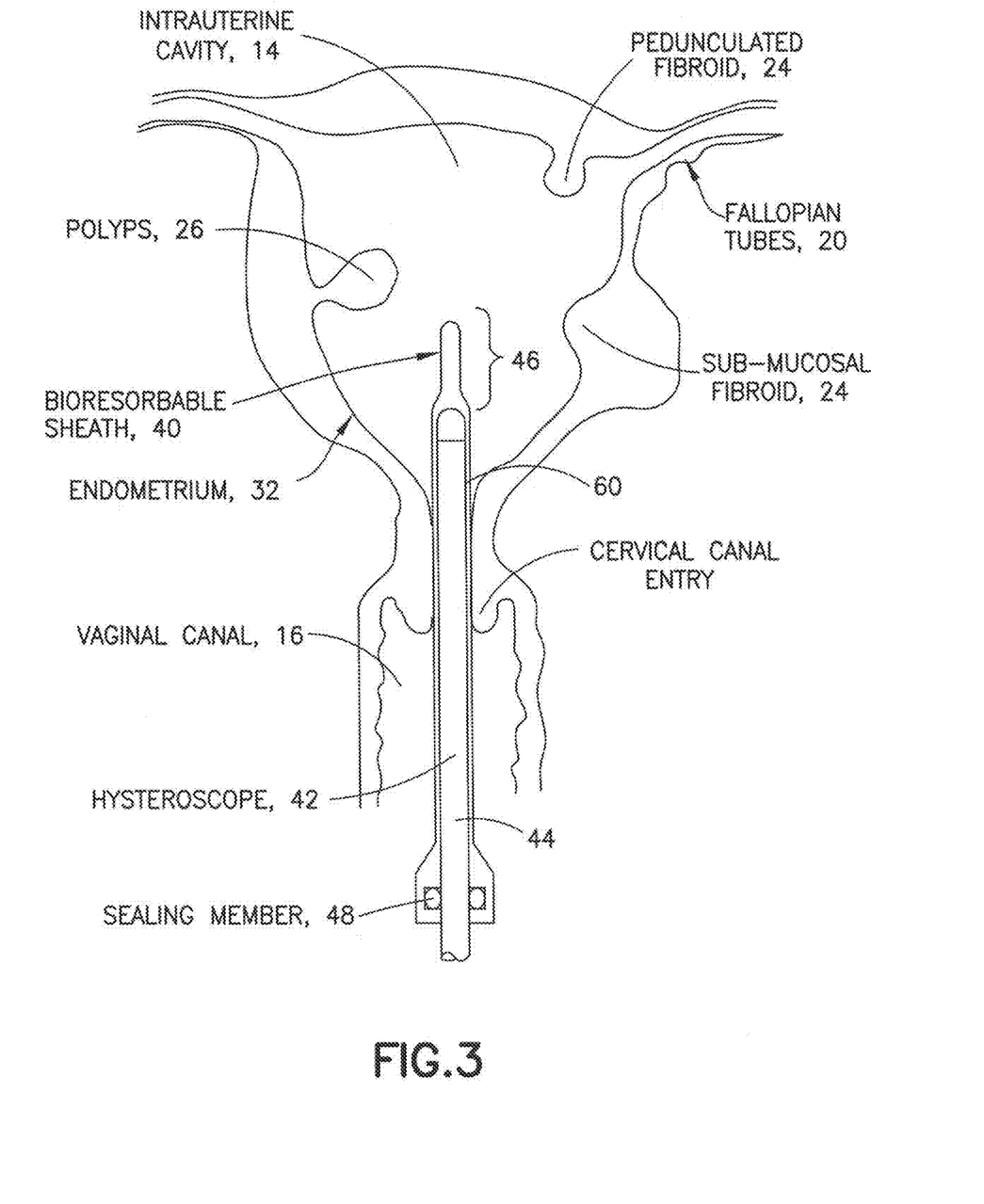
FIG. 3 is a schematic representation of a uterine cavity biocompatible seal on an access sheath inserted into a uterine cavity.

Referring now to FIG. 3, a uterine cavity biocompatible seal is designated generally by the reference number 40 and is hereinafter referred to as "seal 40." The seal 40 is generally applied via an access sheath 60 using an endoscope such as a hysteroscope 42 in a hysteroscopic procedure, the access sheath 60 providing access to the seal 40 and access to the distal end of the hysteroscope 42 being through a working channel 44. The access sheath 60 may also operate to dilate the cervical canal. The seal 40 may be positionable in a uterine cavity in a deflated condition and subsequently inflated by distension fluid or gas instilled into the seal 40. As shown, the seal 40 is a biocompatible member fabricated of a material capable of being broken down and not requiring mechanical removal from the uterine cavity 14 (like sutures and chlorhexhidine chips). In some embodiments, the biocompatible member may be fabricated of a material that is bioresorbable, thus allowing the material to be resorbed into the patient's body. In the alternative, the material of the biocompatible member may be mechanically removable from the uterine cavity 14, either by piecewise extraction or by being dissolved (for example, based on pH, enzymes, or temperature). Materials from which the biocompatible member may be fabricated include, but are not limited to, chitosan, cellulose, collagen, elastin, gelatin, keratin, polyethylene glycol (PEG), polyvinyl alcohol (PVA), combinations of the foregoing, and the like. Procedures used for the manufacture of the biocompatible member as the seal 40 include, but are not limited to, lyophilization, injection molding, UV crosslinking, chemical crosslinking (acid/base), and the like.

When deflated, the seal 40 is received over a distal end of the access sheath 60 on the hysteroscope 42, which comprises the working channel 44 through which the hysteroscopic procedures may be carried out. The seal 40 comprises a forward inflation/expansion zone 46 at a forward end and is configured to be sealed to the access sheath 60 proximate a rearward end using a sealing member 48. Upon initiation of, for example, a hysteroscopic procedure involving the removal of a fibroid 24 or polyp 26, the access sheath 60 is inserted into uterine cavity 14 trans-cervically, and the seal 40 is insufflated with $CO_2$ or other appropriate gaseous medium. The inflation/expansion zone 46, while deflated, can be used to dilate the cervix during initial insertion.

Figures 4, 5:
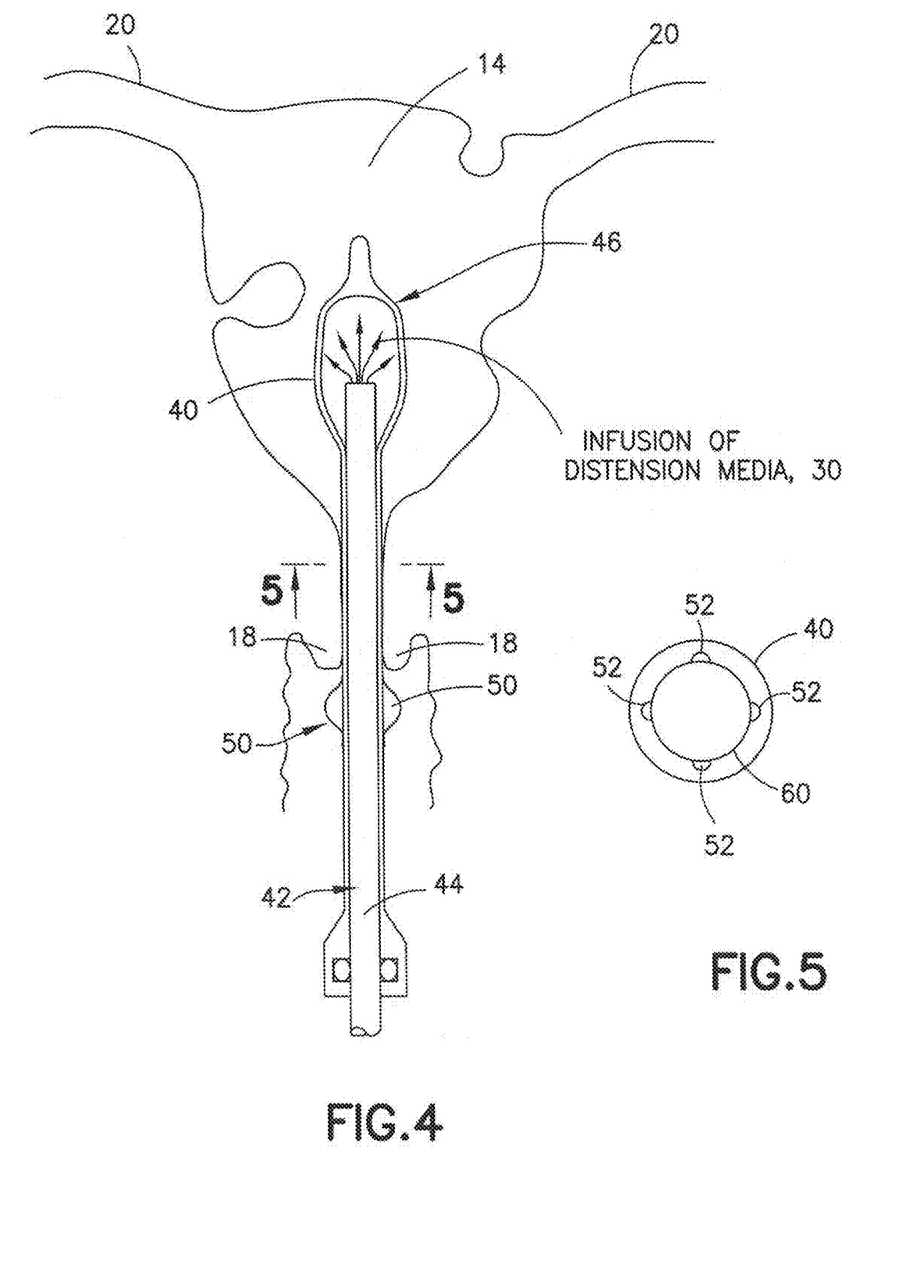
FIG. 4 is a schematic representation of the uterine cavity biocompatible seal partially inflated.
FIG. 5 is cross sectional view of the uterine cavity biocompatible seal on the access sheath.

Referring now to FIG. 4, the material of the biocompatible member is sufficiently elastic to allow the seal 40 to begin to inflate upon infusion of the distension fluid (fluid medium 30). Expansion of the seal 40 allows the outer surface to expand and coat or otherwise engage inside surfaces of the uterine cavity 14 with minimal pressure equivalent to or below the patient's MAP that will provide suitable distension to allow for visualization of the uterine cavity 14. As the seal 40 begins to inflate, a portion 50 of the seal 40 at the external os of the cervix 18 may expand.

Referring to FIG. 5, infusion of the fluid medium 30 may be through a number of distension fluid/gas runners 52 that extend along an outer surface of the access sheath 60. Although four distension fluid/gas runners 52 are shown, any suitable number of distension fluid/gas runners 52 may be used.

Figure 6:
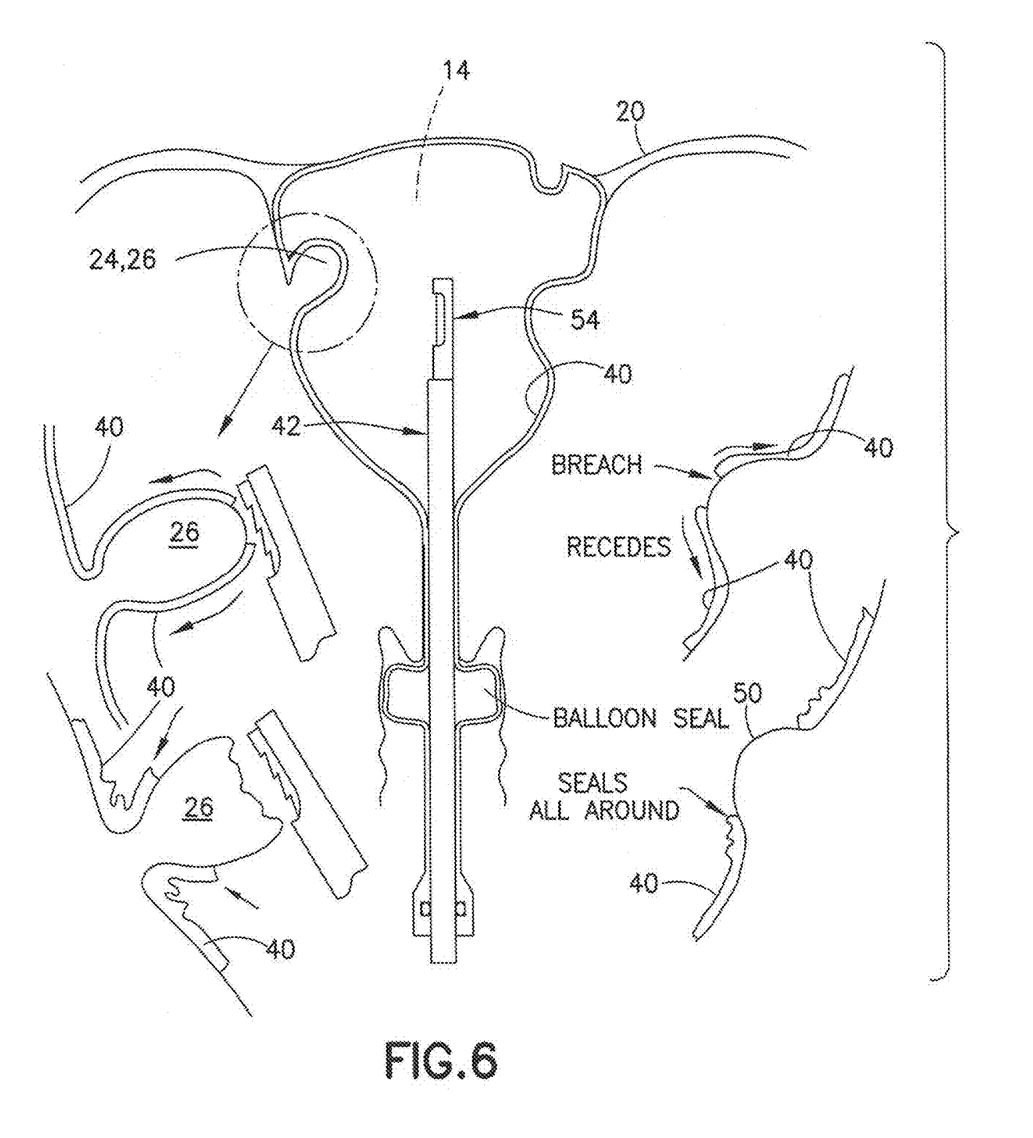
FIG. 6 is a schematic representation of the uterine cavity biocompatible seal fully inflated and disposed on the interior walls of the uterine cavity.

Referring to FIG. 6, once expanded, the material of the seal 40 follows the contours of the walls of the uterine cavity 14 and expands around any protrusions from abnormalities such as submucosal fibroids 24 and polyps 26 while blocking pathways through the fallopian tubes 20. Once expanded, the material of the seal 40 has surface friction with the walls of the uterine cavity 14. The thickness of the material of the seal 40 is such that the seal 40 is transparent or minimally translucent to visually reveal abnormal tissue desired for resection by a tissue removal device 54 inserted through the working channel 44.

Still referring to FIG. 6, the tissue removal device 54 penetrates the material of the seal 40 before resecting the fibroids 24 and/or polyps 26. Once the material of the seal 40 is breached, adjacent surfaces of the material (which is elastic) recede due to contraction (reverse expansion) and overcome the friction between the seal 40 and the walls of the uterine cavity 14, thereby exposing the tissue abnormality for further resection while maintaining a seal around the exposed portion of the tissue to be resected. The breached material of the seal 40 may be extracted via a suction path of the tissue removal device 54 through the working channel 44. Upon completion of the hysteroscopic procedure, the fluid medium 30 is extracted through the working channel 44, the uterine cavity 14 is thereby deflated, and the hysteroscope 42 and (optionally) remaining biocompatible material of the seal 40 is removed. The access sheath 60 is also removed.

Figure 7A:
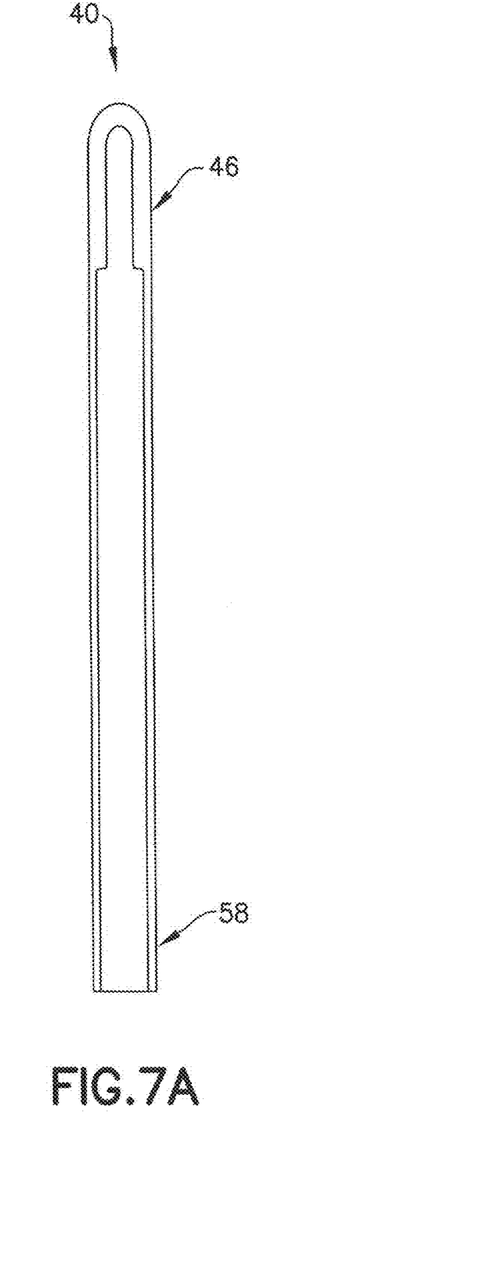
FIG. 7A is a side view of the uterine cavity biocompatible seal sheath fully deflated.

Referring to FIGS. 7A through 7D, the component parts and assembly method are illustrated. As shown in FIG. 7A, material of the seal 40 in the inflation/expansion zone 46 may be thicker than the material at other portions (such as a rearward end 58) of the seal 40.

Figure 7B:
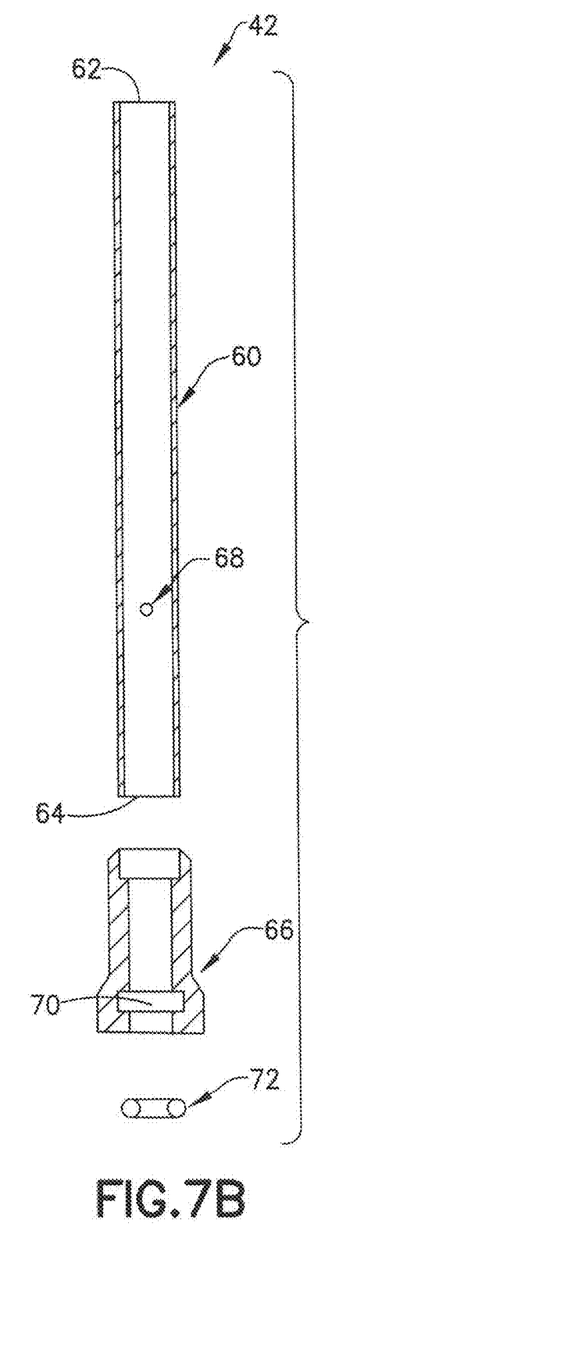
FIG. 7B is a side sectional and exploded view of the access sheath for use with the uterine cavity biocompatible seal.

As shown in FIG. 7B, an elongated tubular member may define the access sheath 60 as having a forward opening 62 through which the fluid medium 30 may be expelled to inflate the seal 40. The access sheath 60 may also have a rearward end 64 on which an end cap 66 may be attached to clamp the seal 40. The access sheath may be an extruded non-metallic tube and may also include fluid exit ports 68 through which the fluid medium 30 may be expelled to expand middle portions of the seal 40 (for example, at the external os of the cervix). The attachment of the end cap 66 to the access sheath 60 may be via a glued joint or an ultrasonic weld on an outer surface of the access sheath 60. The end cap 66 may include a groove 70 machined on an inner surface thereof to accommodate an O-ring 72 to provide a seal point between the end cap 66 and a portion of the hysteroscope 42 extending rearward to the surgeon.

Figure 7C:
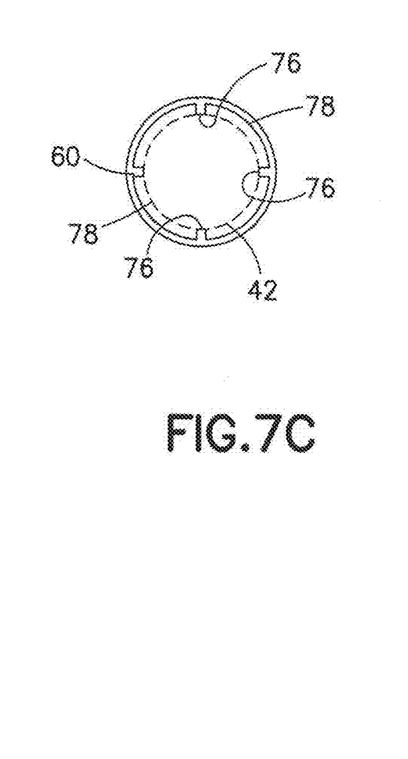
FIG. 7C is a cross sectional view of the forward end of the access sheath of FIG. 7B.

As shown in FIG. 7C, ribs 76 may be located on an inner surface of the access sheath 60. Ribs 76 may operate to center the hysteroscope 42 in the access sheath 60 and may provide annular areas 78 for the flow of the fluid medium 30.

Figure 7D:
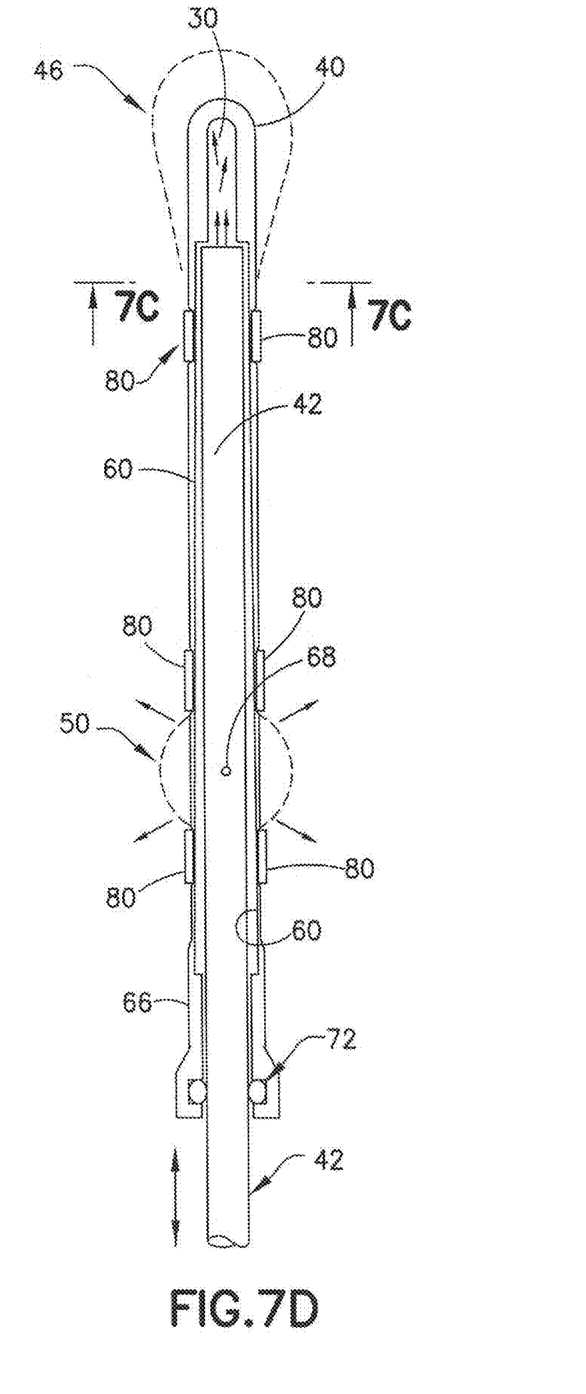
FIG. 7D is a side sectional view of the assembled hysteroscope with the uterine cavity biocompatible seal and the access sheath.

As shown in FIG. 7D, the seal 40 may be received over the forward opening 62 of the access sheath 60. Three heat shrink tubes 80 may be positioned over the seal 40 on the access sheath 60 after assembly to maintain the seal 40 in place on the access sheath 60. The two rearward heat shrink tubes 80 may be spaced sufficiently to define the portion 50, which is positioned at the cervical end of the vaginal tract and expands accordingly. The rearmost end of the seal 40 is maintained on the access sheath 60 via the end cap 66.

Figure 8:
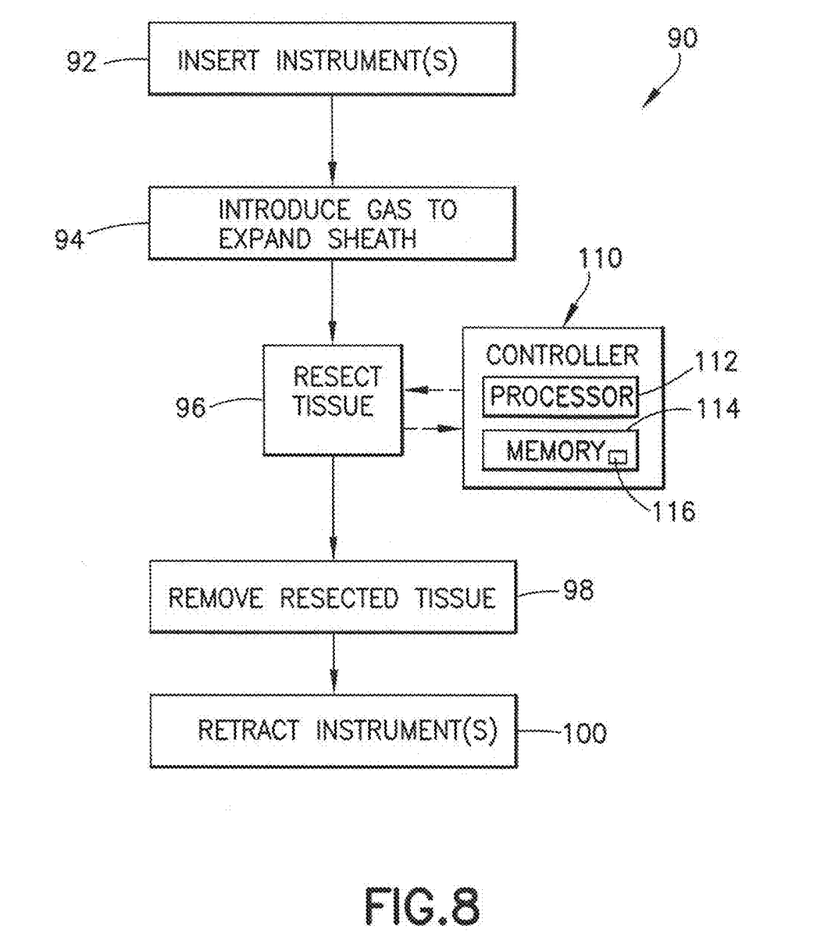
FIG. 8 is a flow of one exemplary embodiment of a method of performing a hysteroscopic procedure using an inflatable biocompatible seal.

Referring to FIG. 8, a flow of one exemplary method of using the seal 40 and the access sheath 60 in conjunction with a hysterocope 42 and also in conjunction with, for example, a tissue removal device 54 is shown generally at 90 and is hereinafter referred to as "method 90." In the method 90, the seal 40 and the access sheath 60 are installed onto the hysteroscope 42 and inserted into the uterine cavity 14, in a step 92. After insertion, the fluid medium 30 may be introduced, in a step 94, through the working channel 44 of the hysteroscope 42 to inflate the seal 40. Instruments that also may be introduced include, but are not limited to, viewing instruments such as cameras and lighting equipment having working channels for the introduction of further instruments such as tissue removal device blades, fluid flow devices, and the like. After inserting the instruments, tissue may be resected in a resection step 96. In a removal step 98, the resected tissue may be removed through a suction path of the tissue removal device blade. Following removal of the resected tissue, the instruments may be retracted in a retraction step 100.

Any of the foregoing step may be carried out using a robot or robotic apparatus and controlled using a controller 110 having a processor 112 and a memory 114, the memory 114 having software 116. Although the resection step 96 is shown as being controlled using the controller 110, it should be understood that any of the described steps could be carried out robotically and using the controller 110.

Referring to all the Figures, the proposed invention provides a seal in the uterine cavity by implementing a coating or lining on the wall of the uterine cavity to block the pathway into the fallopian tubes to prevent saline (or other fluid) spillage to the abdominal cavity. The seal also minimizes the uterine cavity exposure to saline or fluids (such as gases or other distending media) thereby minimizing the extravasation/intravasation of fluids or gas during a hysteroscopic procedure. Furthermore, the seeding of other structures with cancerous or precancerous cells may be avoided. Additionally, accidental perforation of the uterine endometrium wall may be prevented.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

In one exemplary embodiment, a device comprises: an access sheath comprising a tubular member; an inflatable member coupled to the access sheath; and an endoscope having a working channel, the endoscope being configured to be positioned through the access sheath. The inflatable member is configured to be received into a body cavity, such as a uterine cavity, by insertion of the access sheath into the uterine cavity, and the inflatable member is configured to expand to cover a contour of the uterine cavity upon inflation and to internally seal the uterine cavity.

The inflatable member may comprise a biocompatible member. The biocompatible member may be fabricated from one or more of chitosan, cellulose, collagen, elastin, gelatin, keratin, and polyethylene glycol. The inflatable member, once expanded to cover a contour of the uterine cavity, may be one of transparent and translucent to allow an abnormality to be viewed therethrough. The endoscope may be a hysteroscope.

In another exemplary embodiment, a method comprises: delivering a biodegradable expandable member into a uterine cavity of a patient; insufflating the biodegradable expandable member in the uterine cavity to expand the uterine cavity; sealing the biodegradable expandable member against an inner wall of the uterine cavity to seal the uterine cavity internally; and delivering an endoscope into the uterine cavity.

Delivering a biodegradable expandable member into a uterine cavity may comprise inserting an access sheath and the biodegradable expandable member into the uterine cavity from the endoscope. Insufflating the biodegradable expandable member in the uterine cavity may comprise inflating the biodegradable expandable member in the uterine cavity with a gas. The method may further comprise maintaining a mean arterial pressure of the patient lower than a pressure of the gas. The method may further comprise breaching the biodegradable expandable member and resecting an abnormality of the uterine cavity. The method may further comprise allowing at least a portion of the biodegradable expandable member to resorb into the uterine cavity of the patient. The method may further comprise removing at least a portion of the biodegradable expandable member from the uterine cavity.

In another exemplary embodiment, a method of treating a uterine abnormality of a patient comprises: inserting an access sheath having an inflatable member into a uterine cavity while installed to an endoscope, the endoscope having a working channel for fluid inflow; inflating the inflatable member to expand the inflatable member and to cover a contour of the uterine cavity; and operating a medical device through the working channel of the endoscope to treat the uterine abnormality of the patient.

Inserting an access sheath having an inflatable member into a uterine cavity may further comprise dilating an opening into the uterine cavity. Inflating the inflatable member to expand the inflatable member may comprise instilling a fluid medium into the inflatable member. Instilling a fluid medium into the inflatable member may comprise maintaining a pressure of the fluid medium below a mean arterial pressure of the patient. Inflating the inflatable member to expand the inflatable member and to cover a contour of the uterine cavity may comprise sealing the uterine cavity from an interior thereof. Operating a medical device, for example a tissue removal device blade, through the working channel of the endoscope may comprise breaching the inflated inflatable member covering a contour of the uterine cavity and resecting tissue of the uterine abnormality. Breaching the inflated inflatable member at the uterine abnormality may cause the breached inflatable member to recede from around the uterine abnormality to expose the uterine abnormality. The method may further comprise allowing at least a portion of the inflatable member to resorb into the patient.

It should be understood that the foregoing description is only illustrative of the invention. Various, alternatives and modifications can be devised by those skilled in the art without departing from the invention. Accordingly, the invention is intended to embrace all such alternatives, modifications, and variances which fall within the scope of the appended claims.

What is claimed is:

1. A device, comprising:
an access sheath comprising a tubular member; and
an inflatable member coupled to a rearward end of the access sheath, extending along an intermediate portion of the access sheath, and covering a distal end of the access sheath, the inflatable member including a distal expansion portion adjacent to the distal end of the access sheath and an intermediate expansion portion adjacent to the intermediate portion of the access sheath;
wherein the inflatable member is configured to be received into a uterine cavity by insertion of the access sheath through a cervical canal and into the uterine cavity, wherein the distal expansion portion of the inflatable member is configured to expand to cover a contour of the uterine cavity upon inflation and to internally seal the uterine cavity, and wherein the intermediate expansion portion is configured to expand and form a seal at an entry to the cervical canal.

2. The device of claim 1, wherein the inflatable member comprises a biocompatible member.

3. The device of claim 2, wherein the biocompatible member is fabricated from one or more of chitosan, cellulose, collagen, elastin, gelatin, keratin, polyvinyl alcohol, and polyethylene glycol.

4. The device of claim 1, wherein the inflatable member, once expanded to cover a contour of the uterine cavity, is one of transparent and translucent to allow an abnormality to be viewed therethrough.

5. The device of claim 1, further comprising an endoscope having a working channel, the endoscope being configured to be positioned through the access sheath.
providing an endoscope through the access sheath and into the uterine cavity, the endoscope having a working channel;
inflating the inflatable member to expand the inflatable member and to cover a contour of the uterine cavity; and
operating a medical device through the working channel of the endoscope to treat the uterine abnormality of the patient.

6. The device of claim 5, wherein the endoscope is a hysteroscope.

7. The device of claim 5, further comprising a tissue removal device configured for insertion through the working channel.

8. The device of claim 1, wherein the inflatable member is coupled to the rearward end of the access sheath with a sealing member.

9. The device of claim 1, further comprising one or more fluid/gas runners extending along an outer surface of the access sheath and in communication with the inflatable member.

10. The device of claim 9, comprising a plurality of the fluid/gas runners.

11. The device of claim 1, further comprising a plurality of ribs located on an inner surface of the access sheath, the plurality of ribs configured to align an endoscope or a hysteroscope within the access sheath.

* * * * *

UNITED STATES PATENT AND TRADEMARK OFFICE
CERTIFICATE OF CORRECTION

PATENT NO. : 11,172,815 B2  
APPLICATION NO. : 15/849926  
DATED : November 16, 2021  
INVENTOR(S) : Magno et al.

Page 1 of 1

It is certified that error appears in the above-identified patent and that said Letters Patent is hereby corrected as shown below:

In the Claims

In Column 8, Lines 51-59, in Claim 5, after "sheath.", delete "providing an endoscope through the access sheath and into the uterine cavity, the endoscope having a working channel;
inflating the inflatable member to expand the inflatable member and to cover a contour of the uterine cavity; and
operating a medical device through the working channel of the endoscope to treat the uterine abnormality of the patient."

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*